US 6,616,605 B2

(12) United States Patent
Wright et al.

(10) Patent No.: US 6,616,605 B2
(45) Date of Patent: Sep. 9, 2003

(54) QUADRETRACTOR AND METHOD OF USE

(75) Inventors: John T. M. Wright, Denver, CO (US); David R. Clarke, Cherry Hills, CO (US)

(73) Assignee: Genesee Biomedical, Inc., Denver, CO (US)

( * ) Notice: Subject to any disclaimer, the term of this patent is extended or adjusted under 35 U.S.C. 154(b) by 0 days.

(21) Appl. No.: 09/784,579

(22) Filed: Feb. 15, 2001

(65) Prior Publication Data

US 2002/0111538 A1 Aug. 15, 2002

(51) Int. Cl.⁷ .............................................. A61B 17/02
(52) U.S. Cl. ........................................ 600/233; 128/898
(58) Field of Search ................................ 600/201, 215, 600/219, 224, 227, 233, 235; 128/898

(56) References Cited

U.S. PATENT DOCUMENTS

| | | | |
|---|---|---|---|
| 2,053,868 A | * | 9/1936 | Grosso .......................... 600/233 |
| 2,473,266 A | * | 6/1949 | Wexler .......................... 600/215 |
| 3,965,890 A | * | 6/1976 | Gauthier ........................ 403/79 |
| 4,434,791 A | * | 3/1984 | Darnell ......................... 600/233 |
| RE32,021 E | * | 11/1985 | Scott, Jr. ...................... 600/217 |
| 5,728,046 A | * | 3/1998 | Mayer et al. ................... 600/210 |
| 5,951,467 A | * | 9/1999 | Picha et al. ................... 600/206 |
| 5,967,973 A |  | 10/1999 | Sherts et al. .................. 623/233 |
| 6,042,596 A |  | 3/2000 | Bonutti ......................... 606/190 |
| 6,074,343 A | * | 6/2000 | Nathanson et al. ............. 600/214 |
| 6,102,854 A |  | 8/2000 | Cartier et al. .................. 600/228 |
| 6,113,535 A |  | 9/2000 | Fox et al. ...................... 600/228 |
| 6,159,201 A |  | 12/2000 | Hamilton et al. .............. 600/201 |
| 6,162,172 A |  | 12/2000 | Cosgrove et al. .............. 600/208 |
| 6,199,556 B1 | * | 3/2001 | Benetti et al. ................. 128/898 |

* cited by examiner

Primary Examiner—Cary E. O'Connor
(74) Attorney, Agent, or Firm—Swanson & Bratschun LLC

(57) ABSTRACT

A surgical retractor includes a frame and hinges associated with the frame for making the frame conformable to the chest or other anatomical structure of a patient. Retractor blades are operatively associated with the frame for retracting soft tissue or bone structure. Where the surgical retractor includes opposing pairs of retractor blades for retracting soft tissue or bone structure in two relatively generally perpendicular directions, a method of using the device includes making an incision in the skin of a patient, placing the device over the incision, using one opposing pair of retractor blades to retract skin and soft tissue in a first direction and using the second opposing pair of retractor blades to retract bone in a second direction, the second direction being generally perpendicular to the first direction.

21 Claims, 2 Drawing Sheets

QUADRETRACTOR AND METHOD OF USE

FIELD OF THE INVENTION

This invention relates to surgical retractors generally of the type that include a rack and pinion operated pair of retractors for opening a region of the body, often the chest cavity, to provide access for performing surgery and to methods of performing such surgery.

BACKGROUND OF THE INVENTION

Surgery for the correction of congenital defects in infants is a well-known but difficult procedure. Coarctation of the aorta, an abnormal narrowing which may severely inhibit blood circulation, especially in infants, may require surgical correction. It is, of course, important to provide adequate exposure of the aorta in this type of surgery with minimum trauma to the patient.

Similarly, correction of congenital defects in the heart per se requires adequate exposure of the heart chambers with minimum trauma.

Traditional retraction methods and retractors are generally unsuitable for these procedures. The heart or aorta are often exposed using a muscle sparing operation.

In repairs of congenital defects of the aorta, the infant or child is placed laying on the right side. An incision is made in the left lateral portion of the upper thorax, such that the incision follows the edges of the muscles, rather than across the muscles. The present practice is to use a first retractor to retract the muscles, then to use a second retractor, placed at right angles to the first retractor and on top of the first retractor to spread the ribs, thus exposing the pleural cavity.

In general, the typical retractor consists of two sternal blades attached, respectively, to a pair of arms. One arm is rigidly attached to a rack containing a single row of gear teeth, and the second arm rigidly fixed to a moving member that is able to slide along the rack. A rotatable handle, hinged to a simple cog gear is contained in the moving member and engages the rack. Rotation of the handle caused the member to move along the rack, thus changing the separation distance between the sternal blades.

In general, prior art retractors spread a surgical opening in only one direction. It is desirable in some instances, especially in pediatric cardiac surgery to be able to retract the same or different layers of muscle or bone structure, e. g. ribs, in different directions to make the surgical area more accessible.

Devices are known in which an incision in tissue is opened in more than one direction, e.g. providing a generally circular orifice. Such devices are described, for example, in U.S. Pat. Nos. 6,042,596 to Bonutti; 6,162,172 to Cosgrove et. al.; and 6,159,201 to Hamilton, et. al. However, devices such as those referred to and other known prior art devices are not useable in surgical procedure for correcting cardiac or aortic congenital defects in infants or children.

It is an object of this invention to provide a retractor that conforms more readily to the anatomy of the patient and to permit retraction of the muscles of an infant in one direction and retraction of ribs in a perpendicular direction to render a surgical site, e.g. the heart or aorta, accessible. The invention may, of course, be used on adults or even on animals in veterinarian practice but it has unique and special applicability to surgery on infants and young children.

SUMMARY OF THE INVENTION

The present invention is, in one embodiment, a surgical retractor that is configured and constructed to be conformable to the chest or other anatomical structure of a patient comprising means for retracting soft tissue or bone structure in two relative generally perpendicular directions.

Preferably it is configured and constructed to be conformable to the chest or other anatomical structure of a patient comprising means for retracting soft tissue or bone structure in two relative generally perpendicular directions and comprises first and second spaced retractor plates each having first and second ends, third and fourth retractor plates hingably connected respectively to the first ends and to the second ends of the first and second spaced retractor plates for angular movement relative to said first and second spaced retractor plates, and a rack and pinion retractor blade assembly mounted on each of the respective retractor plates. The retractor device is constructed and configured to permit reciprocal movement of generally opposed first and second retractor blades and to permitting reciprocal movement of generally opposed third and fourth retractor blades, the direction of reciprocal movement of the third and fourth retractor blades being generally perpendicular to the direction of reciprocal movement of the first and second retractor blades.

In a preferred embodiment, the first and second retractor plates are generally planar and lie generally in the same plane and further comprise means for locking one or both of the third and fourth retractor plates at selected angles of up to about 45° in either direction relative to the plane of the first and second retractor plates.

Preferably, at least two of the blades, and optionally all of the blades, are configured and constructed to define arcuately curved tissue engaging structure.

The tissue engaging structure of the first and second retractor blades may be longer than the tissue engaging structure of the third and fourth retractor blades or, depending on the order used to identify the blades, the tissue engaging structure of the third and fourth retractor blades may be longer than the tissue engaging structure of the first and second retractor blades.

It is preferred that the first and second spaced retractor plates each have first and second ends, the third and fourth retractor plates are hingably connected respectively to the first ends and to the second ends of the first and second spaced retractor plates for angular movement relative to said first and second spaced retractor plates; and a rack and pinion retractor blade assembly is mounted on each of the respective retractor plates, the retractor device being constructed and configured to permit reciprocal movement of generally opposed first and second retractor blades and to permitting reciprocal movement of generally opposed third and fourth retractor blades, the direction of reciprocal movement of the third and fourth retractor blades being generally perpendicular to the direction of reciprocal movement of the first and second retractor blades. It is also preferred that the retractor mechanism be constructed and configured such that the first and second retractor plates are generally planar and lie generally in the same plane and further comprising means for locking one or both of the third and fourth retractor plates at selected angles of 0 degrees and angles of up to about 45° relative to the plane in which the first and second retractor plates lie. Optionally, the tissue engaging structure of the first and second retractor blades may longer than the tissue engaging structure of the third and fourth retractor blades.

In another embodiment, the invention is embodied in a method of performing surgery upon infants and children to correct defects of the heart or aorta and related tissue, comprising making an incision in the left lateral portion of the upper thorax, such that the incision follows the edges of the muscles, placing a single retractor mechanism over the incision, said retractor mechanism comprising means for retracting soft tissue in one direction and retracting bone structure in a generally perpendicular direction, retracting soft tissue in a first direction, and retracting rib tissue in a second direction generally perpendicular to the first direction.

The inventive concept also includes the method of performing surgery to correct defects of the heart and related tissue comprising making a minimal skin incision over the sternum, placing a single retractor mechanism over the incision, said retractor mechanism comprising means for retracting skin and underlying soft tissue in one direction and retracting bone structure in a generally perpendicular direction, using said mechanism to retract skin and soft tissue in a first direction, making an incision through the sternum or a portion of the sternum, and using the mechanism to retract the sternal bone in a second generally direction, the second direction being generally perpendicular to the first direction.

The method of may include the use of the structures and alternatives described above and in more detail hereinafter.

DESCRIPTION OF THE PREFERRED EMBODIMENT

The figures illustrate and the description that follows relate to an exemplary embodiment of the invention, and do not limit the scope of the invention. For example, the device may be made of stainless steel or any physiological acceptable and mechanically stable material. While the exemplary device provides to sets of retractors oriented relative to each other at right angles, any angular orientation may be used. U-shaped retractor blades and conventional rack and pinion structure are illustrated but any configuration of these elements and assemblies may be used.

Figure 1:
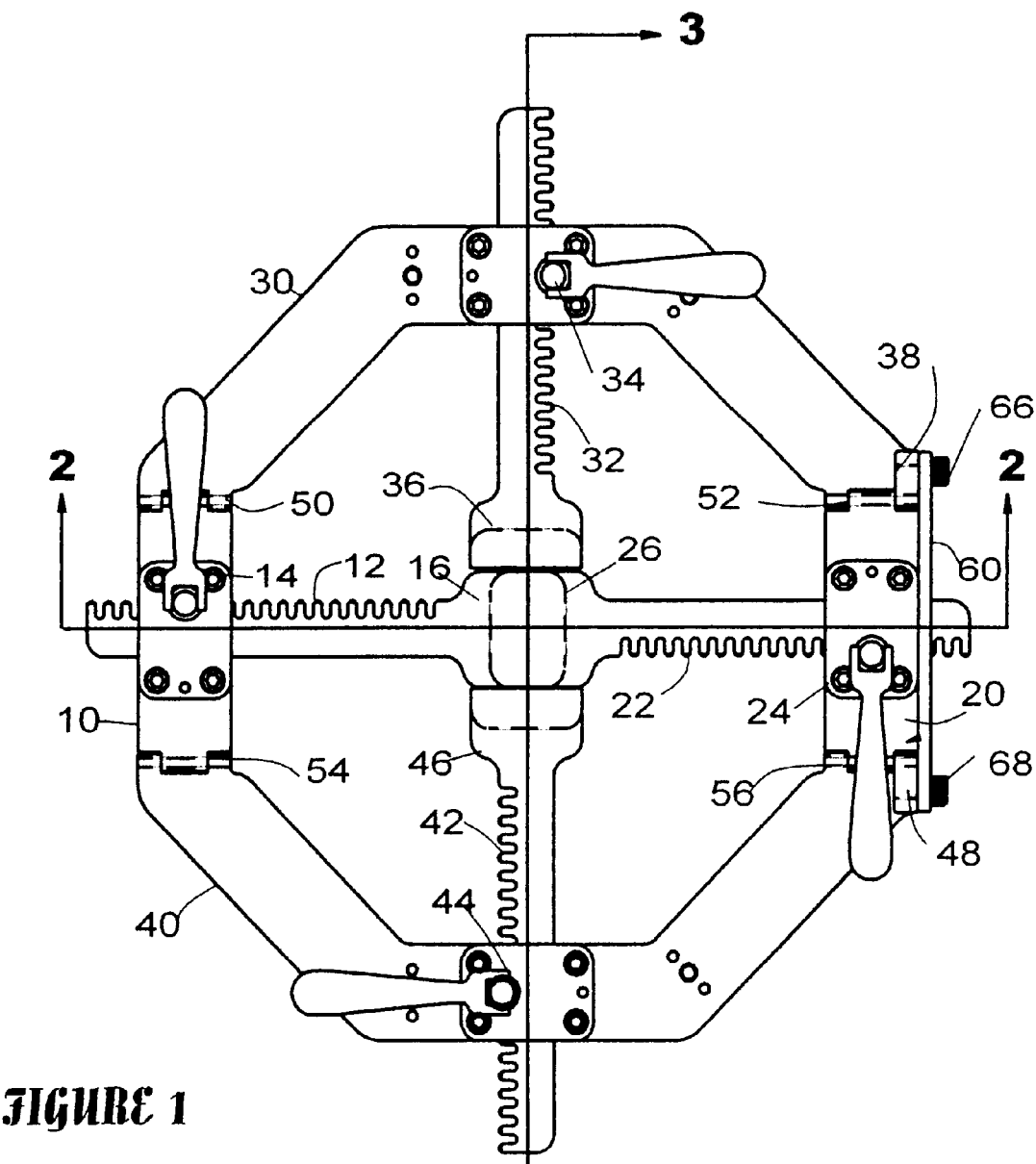
FIG. 1 is a top plan view depicting the overall construction of an exemplary embodiment of the invention.
Figure 2:
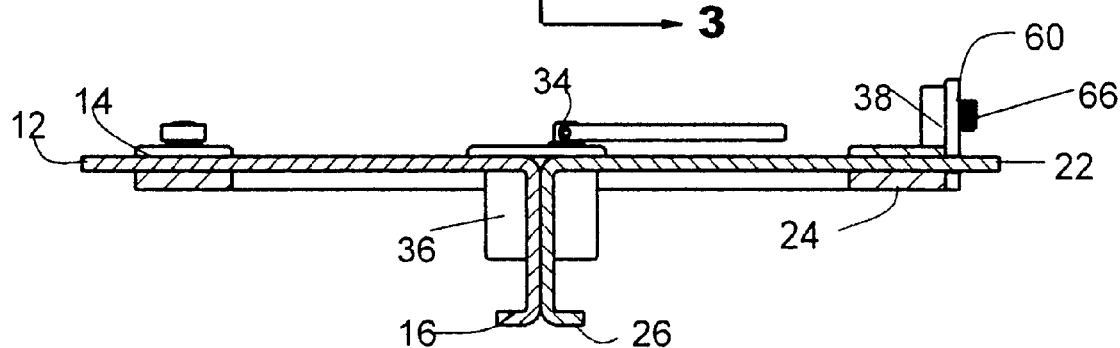
FIG. 2 is a side elevational view of the device depicted in FIG. 1, shown in partial cross-section, taken on the center line in the direction of the arrows indicated by at section line 2—2 in FIG. 1.
Figure 3:
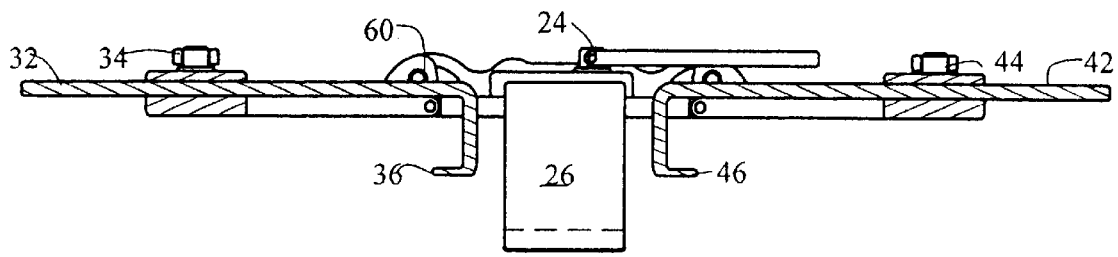
FIG. 3 is a side elevational view of the device depicted in FIG. 1, shown in partial cross-section, taken on the center line in the direction of the arrows indicated by at section line 3—3 in FIG. 1.

Referring to FIG. 1 first, the retractor of this invention, called a quadretractor because it embodies four independent retractor assemblies, comprises first and second retractor plates 10 and 20 spaced, in the preferred embodiment, apart from each other and lying perpendicular to a line 2—2 of the device. The quadretractor also comprises third and fourth retractor plates 30 and 40 portions of which, in the preferred embodiment, are spaced apart from each other and are perpendicular to a second line 3—3 of the device, the second line being, in the preferred embodiment, perpendicular to the first line. These angular relationships are not critical to the invention, however. Lines 2—2 and 3—3 are, in this embodiment, center lines but the first and second lines need not be center lines.

In the preferred embodiment, the first and second retractor plates are rectangular plates with hinge elements at their ends. The third and fourth retractor plates comprise center portions which lie perpendicular to the line 3—3 and spacing portions connecting at the proximal ends to the center portion and having hinge elements at the distal ends. The retractor plates are, respectively, unitary structures in the device as shown, but unitary structure is not required.

The quadretractor comprises two sets of opposed retractor blades on racks, each of which is reciprocally driven by a pinion assembly.

The quadretractor comprises a first rack and pinion blade assembly comprising rack 12, pinion 14 and blade 16, mounted for reciprocal movement on first retractor plate 10 and second rack and pinion blade assembly comprising rack 22, pinion 24 and blade 26, mounted for reciprocal movement on first retractor plate 20. The first and second blades 16 and 26 move apart relative to each other for engaging and separating portions of the patient's tissue and or bone in a first direction.

Figure 5:
FIG. 5 is a top plan view of a portion of an alternative embodiment of one of the blades of the retractor in which the tissue engaging surface is curved. In the drawing, the curve is an arc of a circle, but other arcs or curves may be used.
Figure 6:
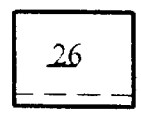
FIG. 6 is an elevational view of the end of the tissue engaging structure of the alternative embodiment shown in FIG. 5 illustrating a shorter tissue engaging structure of this embodiment. In practice the engaging structure for the ribs may be longer than the engaging structure for soft tissue.

The quadretractor also comprises a third rack and pinion blade assembly comprising rack 32, pinion 34 and blade 36, mounted for reciprocal movement on third retractor plate 30 and fourth rack and pinion blade assembly comprising rack 42, pinion 44 and blade 46, mounted for reciprocal movement on first retractor plate 40, The third and fourth blades 36 and 46 move apart relative to each other for engaging and separating portions of the patient's tissue and or bone in a second direction which, in the preferred embodiment, is perpendicular to the first direction. Upstanding locking tabs 38 and 48, respectively, are provided on the third and fourth retractor plates are provided also, the function of which is described hereinafter. Any or all of the blades may be configured and constructed to provide for curved structure for engaging the muscles, ribs or other tissue, as shown in FIGS. 5 and 6 which depict an exemplary form of the blade. In this exemplary embodiment, the curve is an arcuate curve but the curve need not be an arc in the mathematical sense. The tissue engaging structure, the portion extending away from the rack, is shorter than that depicted in FIG. 1, illustrating the concept that the soft tissue engaging structure may be shorter than the rib tissue engaging structure.

Figure 4:
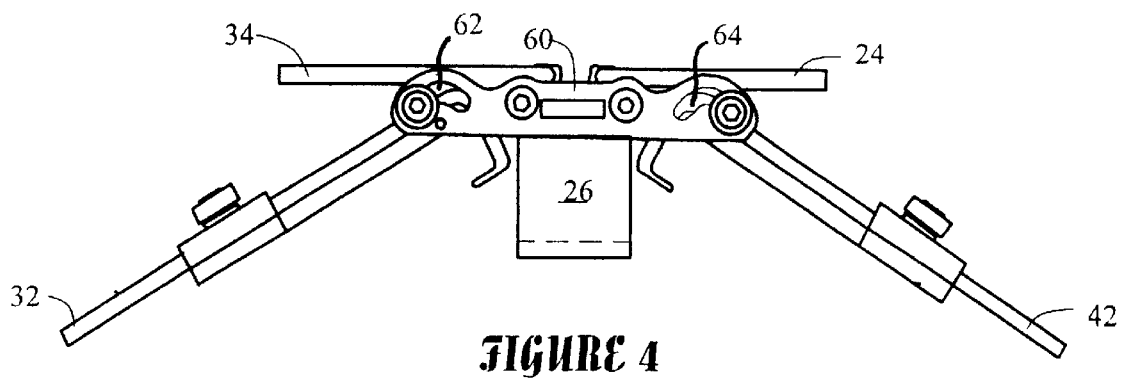
FIG. 4 is a side elevational view of the device depicted in FIG. 1 taken from the right side of FIG. 1, depicting both of the hinged retractor frame members 45° downwardly from the remainder of the device as depicted in FIG. 3 to illustrate an example of the possible orientation and arrangement of the members of the device relative to each other.

Hinges 50 and 52 connect the third retractor plate to ends of the first and second retractor plates for permitting the third retractor plate to pivot upwardly or downwardly, as depicted in FIG. 4, from the plane of the first and second retractor plates. Likewise, hinges 54 and 56 connect the third retractor plate to other ends of the first and second retractor plates for permitting the third retractor plate to pivot upwardly or downwardly, as depicted in FIG. 4, from the plane of the first and second retractor plates. In FIG. 4, to which reference is now specifically made, the fourth retractor plate is pivoted upwardly relative to the plane of the first and second retractor plates. It will now be clear that the third and fourth retractor plates can be pivoted on the hinges to any angle from 0 degrees to 90 degrees relative to the plane in which the first and second retractor plate lies.

The angular orientation of the third and fourth retractor plates may be fixed by means of and upstanding locking portion 60 on one of the first and second retractor plates which are constructed to define arcuate slots 62 and 64 through which screws 66 and 68 extend and are threadably received in apertures in upstanding locking tabs 38 and 48, respectively, on the third and fourth retractor plates. When the respective screws are tightened, the angular orientation of the third and fourth retractor plates, and of the third and fourth retractor blades, relative to the first and second retractor plates is fixed.

Two specific methods are disclosed, being the more common expected uses of the retractor mechanism described above.

The invention is embodied in a method of performing surgery upon infants and children to correct defects of the heart or aorta and related tissue, comprising making an incision in the left lateral portion of the upper thorax, such that the incision follows the edges of the muscles, placing a single retractor mechanism over the incision, said retractor mechanism comprising means for retracting soft tissue in one direction and retracting bone structure in a generally perpendicular direction, retracting soft tissue in a first direction, and retracting rib tissue in a second direction generally perpendicular to the first direction.

The inventive concept also includes the method of performing surgery to correct defects of the heart and related tissue comprising making a minimal skin incision over the sternum, placing a single retractor mechanism over the incision, said retractor mechanism comprising means for retracting skin and underlying soft tissue in one direction and retracting bone structure in a generally perpendicular direction, using said mechanism to retract skin and soft tissue in a first direction, making an incision through the sternum or a portion of the sternum, and using the mechanism to retract the sternal bone in a second generally direction, the second direction being generally perpendicular to the first direction.

It is preferred that the first and second spaced retractor plates each have first and second ends, the third and fourth retractor plates are hingably connected respectively to the first ends and to the second ends of the first and second spaced retractor plates for angular movement relative to said first and second spaced retractor plates; and a rack and pinion retractor blade assembly is mounted on each of the respective retractor plates, the retractor device being constructed and configured to permit reciprocal movement of generally opposed first and second retractor blades and to permitting reciprocal movement of generally opposed third and fourth retractor blades, the direction of reciprocal movement of the third and fourth retractor blades being generally perpendicular to the direction of reciprocal movement of the first and second retractor blades. It is also preferred that the retractor mechanism be constructed and configured such that the first and second retractor plates are generally planar and lie generally in the same plane and further comprising means for locking one or both of the third and fourth retractor plates at selected angles of 0 degrees and angles of up to about 45° relative to the plane in which the first and second retractor plates lie. Optionally, the tissue engaging structure of the first and second retractor blades may longer than the tissue engaging structure of the third and fourth retractor blades.

It will now be seen that the quadretractor is conformable to the chest or other anatomical structure of virtually any patient and provides means for retracting soft tissue or bone structure in two generally perpendicular directions, although perpendicularity is not critical.

INDUSTRIAL APPLICATION

This invention is useful in the medical profession and in the medical device industry.

What is claimed is:

1. A surgical retractor comprising;

a frame;

means operatively associated with the frame for making the frame conformable to the chest or other anatomical structure of a patient;

first pair of opposing retractor blade assemblies operatively associated with the frame configured in retract soft tissue generally along a first line, the first pair of opposing retractor blade assemblies each having a soft tissue engaging structure of a first length extending transverse the frame; and a second pair of opposing retractor blade assemblies operatively associated with the frame configured to retract bone structure generally along a second line transverse to the first line, the second pair of opposing retractor blades having a bone tissue engaging structure of a length greater than the first length extending transverse the frame.

2. The surgical retractor of claim 1 wherein the first and second lines are relatively generally perpendicualar.

3. A surgical retractor comprising:

first and second opposing retractor plates each having first and second ends, each of the first and second opposing retractor plates residing in generally a single plane; and third and fourth opposing retractor plates hingably connected respectively to the first ends and to the second ends of the first and second spaced retractor plates for angular movement relative the single plane.

4. The retractor of claim 2 further comprising means for locking at least one of the third and fourth retractor plates at selected angles of 0 degrees and angles other than 0 degrees relative to the single plane.

5. The surgical refractor of claim 3 further comprising:

a first pair of retractor blade assemblies; and a slidable connection between each retractor blade assembly of the first pair of retractor blade assemblies and one of 1) each of the first and second opposing retractor plates and 2) each of the third and fourth opposing retractor plates.

6. The surgical refractor of claim 5 wherein the slidable connection comprises a rack and pinion assembly.

7. The surgical retractor of claim 5 further comprising:

a second pair of retractor blade assemblies; and a slidable connection between each retractor blade assembly of the second pair of retractor blade assemblies and the other of 1) each of the first and second opposing retractor plates and 2) each of the third and fourth opposing retractor plates.

8. The surgical retractor of claim 7 wherein the first and second opposing retractor plates, the third and fourth opposing retractor plates, first and second pairs of retractor blade assemblies and the slidable connections are configured to provide slidable novement of the first pair of retractor blade assemblies which is generally perpendicular to slidable movement of the second pair of retractor blade assemblies.

9. The surgical retractor of claim 7 wherein each retractor blade assembly includes a retractor blade and the retractor blades of the first pair of retractor blade assemblies are longer than the retractor blades of the second pair of refractor blade assemblies.

10. In the method of performing surgery to correct defects of the heart or aorta and related tissue, the improvement comprising:

making an incision in the left lateral portion of the upper thorax, such that the incision follows the edges of the muscles;

placing a single retractor mechanism over the incision, said retractor mechanism comprising means for retracting soft tissue in one direction and retracting bone structure in a generally perpendicular direction;

using said mechanism to retract soft tissue in a first direction; and using said mechanism to retract rib tissue in a second direction generally perpendicular to the first direction.

11. The method of claim 10 wherein the retractor mechanism comprises:

first and second spaced retractor plates each having first and second ends;

third and fourth retractor plates hingably connected respectively to the first ends and to the second ends of the first and second spaced retractor plates for angular movement relative to said first and second spaced retractor plates; and a rack and pinion retractor blade assembly mounted on each of the respective retractor plates;

the retractor device being constructed and configured to permit reciprocal movement of generally opposed first and second retractor blades and to permitting reciprocal movement of generally opposed third and fourth retractor blades, the direction of reciprocal movement of the third and fourth retractor blades being generally perpendicular to the direction of reciprocal movement of the first and second retractor blades.

12. The method of claim 11 wherein the retractor mechanism is constructed and configured such that the first and second retractor plates are generally planar and lie generally in the same plane and further comprising means for locking one or both of the third and fourth retractor plates at selected angles of 0 degrees and angles of up to about 45 degrees relative to the plane in which the first and second retractor plates lie.

13. The method of claim 12 wherein the retractor mechanism is configured and constructed such that the tissue engaging structure of the first and second retractor blades is longer than the tissue engaging structure of the third and fourth retractor blades.

14. The method of claim 11 wherein the retractor mechanism is configured and constructed such that the tissue engaging structure of the first and second retractor blades is longer than the tissue engaging structure of the third and fourth retractor blades.

15. In the method of performing surgery to correct defects of the heart and related tissue, the improvement comprising:

making a minimal skin incision over to sternum;

placing a single retractor mechanism over the incision, said retractor mechanism comprising means for retracting skin and underlying soft tissue in one direction and retracting bone structure in a generally perpendicular direction;

using said mechanism to retract skin and soft tissue in a first direction;

making an incision through the sternum or a portion of the sternum; and using said mechanism to retract the sternal bone in a second direction, the second direction being generally perpendicular to the first direction.

16. The method of claim 15 wherein the retractor mechanism comprises:

first and second spaced retractor plates each having first and second ends;

third and fourth retractor plates hingably connected respectively to the first ends and to the second ends of the first and second spaced retractor plates for angular movement relative to said first and second spaced retractor plates; and a rack and pinion retractor blade assembly mounted on each of the respective refractor plates;

the retractor device being constructed and configured to permit reciprocal movement of generally opposed first and second retractor blades and to permitting reciprocal movement of generally opposed third and fourth retractor blades, the direction of reciprocal movement of the third and fourth retractor blades being generally perpendicular to the direction of reciprocal movement of the first and second retractor blades.

17. The method of claim 16 wherein the retractor mechanism is constructed and configured such that the first and second retractor plates are generally planar and lie generally in the same plane and further comprising means for locking one or both of the third and fourth retractor plates at selected angles of 0 degrees and angles of up to about 45o relative to the plane in which the first and second retractor plates lie.

18. The method of claim 17 wherein the retractor mechanism is configured and constructed such that the tissue engaging structure of the first and second retractor blades is longer than the tissue engaging structure of the third and fourth retractor blades.

19. The method of claim 15 wherein the retractor mechanism is configured and constructed such that the tissue engaging structure of the first and second retractor blades is longer than the tissue engaging structure of the third and fourth retractor blades.

20. A surgical retractor comprising:

a first retractor plate defining a first plate;

a second retractor plate defining a second plate;

a retractor blade assembly including a rack and pinion mechanism operatively associated with each retractor plate, the rack and pinion mechanisms being configured to retract tissue in substantially opposite directions; and a hinged connection operatively associated with each of the first and second retractor plates to provide angular movement of the first and second retractor plates relative to each other, whereby the first plane can be transverse the second plane at a select angle.

21. The surgical retractor of claim 20 further comprising locking means for locking the first retractor plate relative to the second retractor plate at a select angle.

* * * * *